United States Patent [19]
Anderson et al.

[11] Patent Number: 5,058,574
[45] Date of Patent: Oct. 22, 1991

[54] THERAPEUTIC LIMB BRACE

[76] Inventors: Lucinda L. Anderson, 2396 Mountain Woods, Colton, Calif. 92324; Christopher D. Anderson, 1250 Root Rd., Modesto, Calif. 95351

[21] Appl. No.: 542,162

[22] Filed: Jun. 22, 1990

[51] Int. Cl.$^5$ .......................... A61F 5/01; A61F 5/00; A61F 5/04
[52] U.S. Cl. ................. 128/80 F; 128/80 R; 128/80 C; 128/80 H
[58] Field of Search ............... 128/77, 80 R, 80 C, 128/80 H, 80 F, 87 R, 88, 80 E; 36/11.5, 7.5, 69, 118, 92, 105, 125

[56] References Cited

U.S. PATENT DOCUMENTS

| | | | |
|---|---|---|---|
| 2,267,848 | 12/1941 | Taylor | 128/80 F |
| 2,573,866 | 11/1951 | Murphy . | |
| 2,772,674 | 12/1956 | Swiech et al. . | |
| 3,805,773 | 4/1974 | Sichau . | |
| 4,370,977 | 2/1983 | Mauldin et al. . | |
| 4,414,965 | 11/1983 | Mauldin et al. | 128/87 R |
| 4,433,679 | 2/1984 | Gautlin et al. | 128/80 F |
| 4,456,003 | 6/1984 | Allard et al. . | |
| 4,489,718 | 12/1984 | Martin . | |
| 4,494,534 | 1/1985 | Hutson | 128/88 |
| 4,624,246 | 11/1986 | Ajemian . | |
| 4,688,559 | 8/1987 | Vito et al. . | |
| 4,817,588 | 4/1989 | Bledsoe | 128/80 C |
| 4,919,118 | 4/1990 | Morris | 128/88 |

FOREIGN PATENT DOCUMENTS

| | | | |
|---|---|---|---|
| 410500 | 12/1909 | France | 36/125 |
| 2447184 | 9/1980 | France | 128/80 C |
| 1489762 | 6/1989 | U.S.S.R. | 128/80 C |
| 2215213A | 9/1989 | United Kingdom | 128/80 C |

OTHER PUBLICATIONS

LMB Rehab Products, Inc. 1988 Catalog, 1988, pp. 1–20.
"Dynamic Elbow Extension Brace" advertisement, Anderson Enterprises, Modesto, Calif., 1 page, no date.
"Dynamic Elbow Brace" flyer, Anderson Enterprises, Modesto, Calif., 2 pages, no date.

Primary Examiner—Richard J. Apley
Assistant Examiner—Karen G. Horowitz
Attorney, Agent, or Firm—Sheldon & Mak

[57] ABSTRACT

A therapeutic limb brace for gradually extending flexion contractures of a patient's knee or elbow, and for increasing dorsiflexion of the foot. Upper and lower frames of the brace are incrementally adjustable in both length and lateral spacing for fitting limbs of various proportions, the frames having side members that are comfortably spaced apart from the limb. Control of knee joint movement, for example, is provided by one or more tension springs that can be selectively hooked in parallel between the upper and middle frames for dynamic therapy, a stop member for preventing hyperextension, and a plurality of index holes that can be used in static therapy for locking the frames in fixed angular relation or for limiting movement to a selected angular range. A turnbuckle substituted for one of the springs provides gradual movement at high mechanical advantage. A cable and sheave tackle assembly having series-connected springs can replace the direct parallel spring connections for simplifying the wearing and adjustment of the brace by the user. A lower frame for controlled foot support has a padded base, front and rear blocks for lateral confinement, and adjustable front, instep and heel straps for holding the foot in place, the heel strap having a cup member for holding the heel down. A plurality of tension spring connections between the middle and lower frames permits dynamic inducement of dorsiflexion; static control is provided by a substituted turnbuckle. An ankle strap provides controlled prevention of either inversion or eversion as needed.

35 Claims, 3 Drawing Sheets

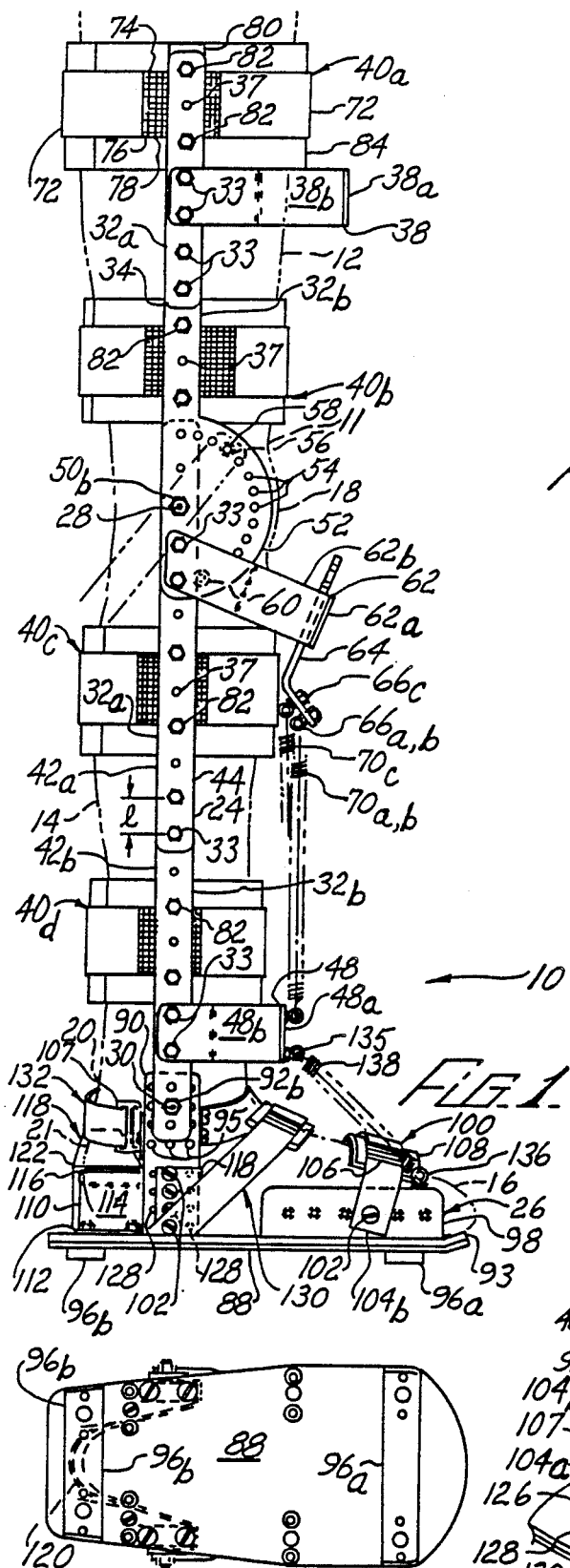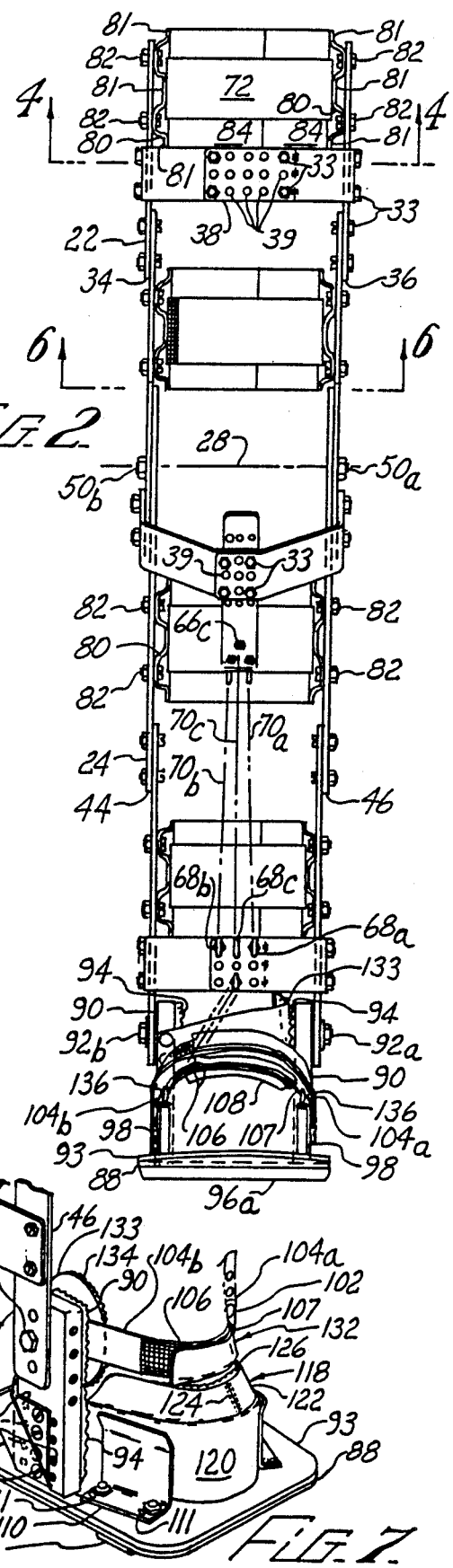

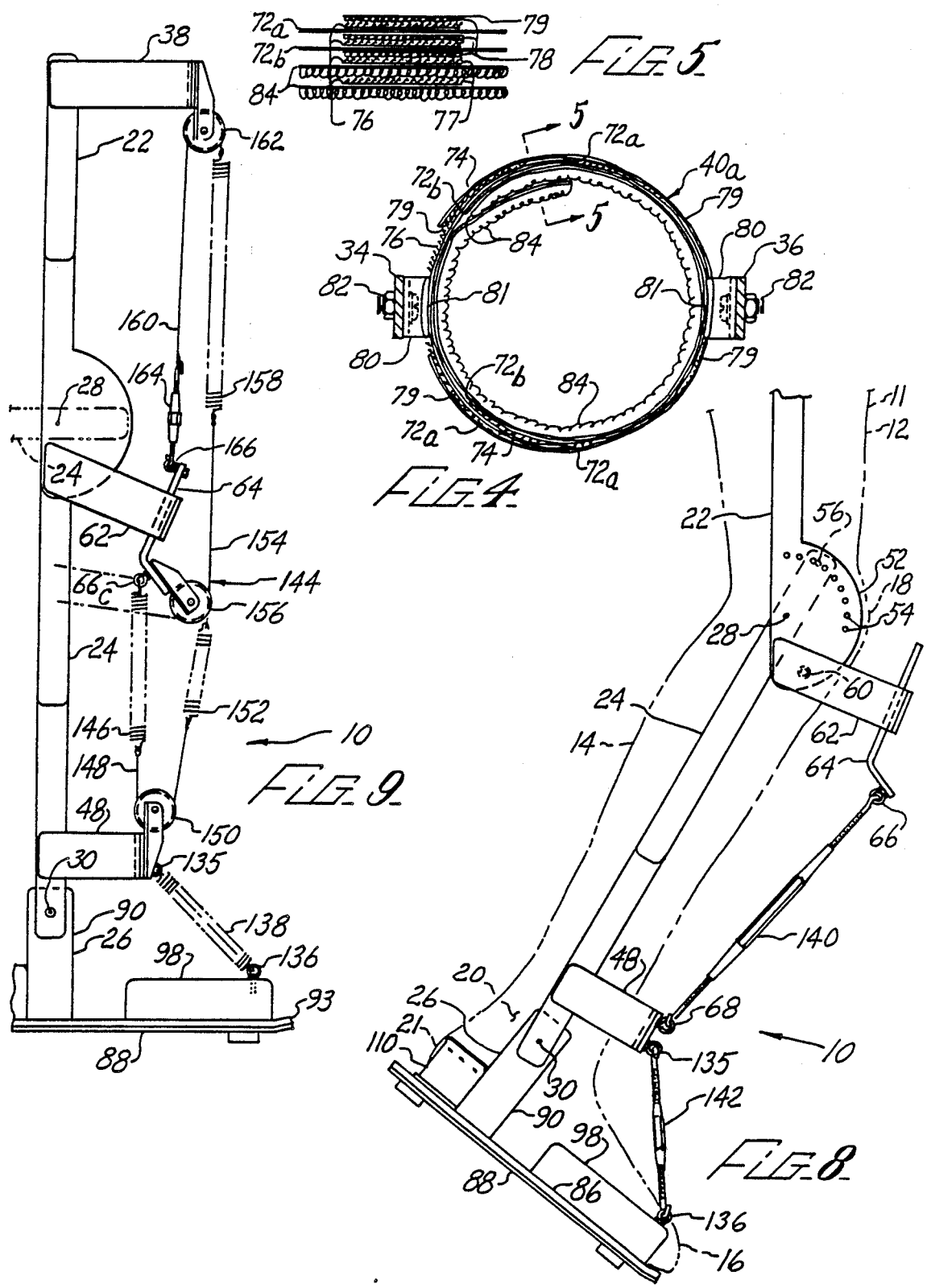

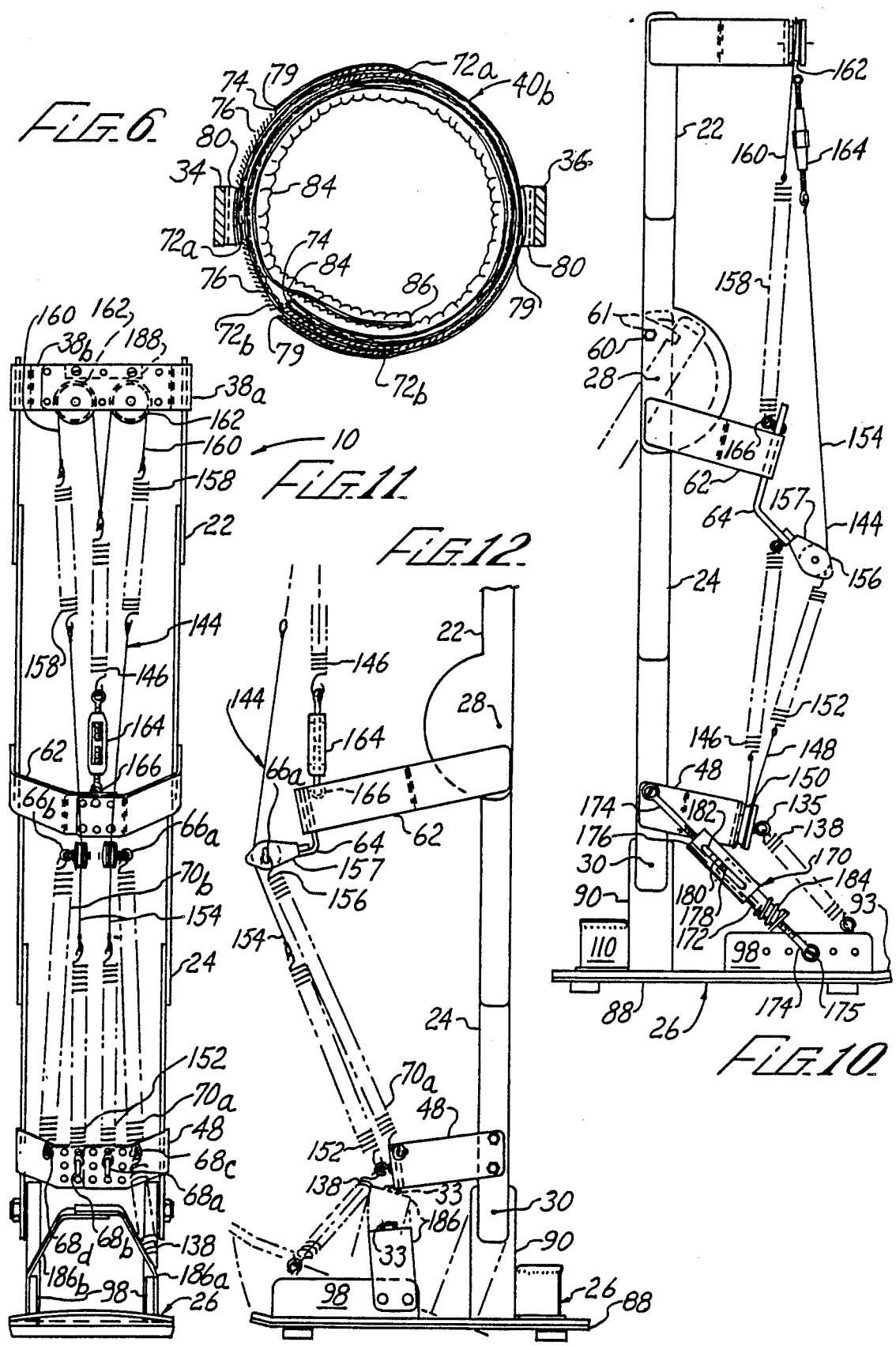

THERAPEUTIC LIMB BRACE

BACKGROUND

The present invention relates to braces used in a clinical setting for rehabilitation of flexion and extension contractures of the knee, ankle, and elbow after neurologic or orthopedic injury.

Braces of the prior art are typically designed for prevention of contractures or immobilization of joints. Conventional braces have metal side frames for positioning along opposite sides of a patient's limb, and a plurality of straps for securing the frames to the limb. The frames have articulated joints for permitting movement of associated limb joints of the patient. The joints can be lockable or equipped with biasing means for resisting movement.

A problem with existing braces is the difficulty in fitting them to varying shapes and sizes of the extremities because the straps are attached directly to the metal framework. This also increases the potential for the development of pressure sores where the frame is pulled into contact with soft tissues.

Another problem is that the braces are generally not suitable for treating existing contractures because they do not exert sufficient force to extend flexion contractures or to rehabilitate to a functional range of motion. Also, in leg braces that include foot support, there is no satisfactory control of inversion or eversion of the foot. Also, existing braces for ambulatory patients (walking braces) use the patient's shoe belted into the brace. Thus it is not practical to wear such braces either with or without a shoe.

Thus there is a need for a brace that not only will statically flex and immobilize and both statically and dynamically extend a user's limb, but will produce a variable dynamic force of a sufficient degree to extend a severe flexion contracture.

SUMMARY

The present invention is directed to an improved adjustable therapeutic brace that meets this need. The brace includes upper and middle frames, each frame having right and left rigid frame portions and each having at least one cross frame member for rigidly connecting the corresponding upper and middle frame portions in parallel spaced relation, and means for connecting the upper and middle frame portions in spaced relation to opposite sides of a user's limb; right and left first hinge means for pivotally connecting the upper frame to the middle frame relative to a first hinge axis, the middle frame being movable from a flexion position to an extension position relative to the upper frame; and first limiting means for selectively limiting movement of the middle frame about the first hinge axis relative to the upper frame. Preferably, at least one of the upper and middle frame portions includes an upper frame member and a lower frame member, and means for selectively rigidly connecting the frame members in overlapping parallel relation for obtaining a desired effective length of the upper and middle frame. Each cross frame portion can include means for selectively defining a separation between opposite sides thereof for adjustably spacing the frame portions from the user's limb portions. The means for connecting the frame portions relative to the user's limb portions can include a plurality of spaced apart limb strap assemblies connected to each of the upper and middle frame portions. Preferably, at least some of the limb strap assemblies include front and rear adjustable buckle means for providing opening and closure of the respective strap assemblies, as well as adjustment of same, selectively from both the front and rear of the user, at least some of the limb strap assemblies each including an adjustable limb strap for enclosing the limb portion, and a pair of anchor straps, each connecting the limb strap to one of the right and left frame portions for support of the limb strap in spaced relation to the frame portions.

The first limiting means can include means for selectively locking the first hinge means into one of a plurality of angularly spaced positions, the means for locking the first hinge means including a plate member fixed on one of the upper and middle frames for forming a plurality of spaced engagement surfaces which can be equidistant from the first hinge axis, and means for locating an engagement member in fixed relation to the other of the upper and middle frames and being in locating engagement with a selected one of the engagement surfaces. Each of the upper frame portions can form one of the plate members, and each of the middle frame portions can include means for locating the corresponding engagement members. The means for locating the engagement members can include an engagement passage in each of the middle frame portions which can be located in line with the upper frame in the extension position, and opposite the first hinge axis from the means for connecting the middle frame portions to the middle limb portion. Each of the engagement surfaces can form a cylindrical passage between opposite sides of one of the frame portions. Preferably, the first limiting means includes means for selectively connecting extension biasing means between the upper frame and the middle frame for urging the middle frame toward the extension position. The means for selectively connecting extension biasing means can include a plurality of eye members rigidly connected to each of the upper frame and middle frame for sequentially connecting a plurality of biasing members therebetween, each of the biasing members providing a portion of a total biasing moment.

The means for selectively connecting extension biasing means can include first sheave means mounted in fixed relation to one of the upper and middle frames and offset from the first hinge axis, a flexible tension member movably engaging the sheave means, a first biasing member connected between the tension member and one of the upper and middle frames, and means for connecting the tension member to the other of the upper and middle frames. The means for selectively connecting extension biasing means can also include second sheave means fixedly located on the other of the upper and middle frames and spaced from the first sheave means, the tension member movably engaging the second sheave means, and a second biasing member connected between the tension member and the one of the upper and middle frames. Preferably, the means for selectively connecting extension biasing means includes turnbuckle means connected in series with the tension member for adjusting an overall length of the tension member and the biasing members of the extension biasing means. Also, the means for selectively connecting extension biasing means can further include third sheave means fixedly located on one of the upper and middle frames, portions of the tension member serially passing over the first, second, and third sheave means.

In another preferred configuration of the means for connecting extension biasing means, there are two parallel connected counterparts of at least the first sheave means, a portion of the tension member, and one of the biasing members.

Preferably, the brace includes stop means for preventing movement of the middle frame beyond a stop extremity angle about the first hinge axis relative to the upper frame. The stop means can include a stop member on one of the upper and middle frames, the stop member engaging the other of the frames in the extension position. The stop means can further include a plate member fixed on one of the upper and middle frames forming a plurality of spaced engagement surfaces, and a stop member for engagement by a selected one of the engagement surfaces for preventing movement of the other frame member in one direction relative thereto by contact therewith.

The brace can further include a lower frame connected to the middle frame and having a base for supporting a limb extremity of the user. Second hinge means can also be included whereby the lower frame is pivotably connected to the middle frame relative to a second hinge axis. An effective length of the middle frame portion is preferably changeable for selecting a desired distance between the first hinge axis and the second hinge axis. The brace can include means for controlling an extremity angular position of the lower frame relative to the middle frame about the second hinge axis. Preferably the means for controlling the lower frame can include coupling means for connecting the lower frame and the middle frame along a coupling axis, the coupling axis being displaced to one side of the second hinge axis and having a connection component in a plane normal to the second hinge axis. The coupling means can include a turnbuckle assembly which is pivotally connected between the lower frame and middle frame for locking the lower frame in a predetermined angular position relative to the middle frame. The coupling means can also include means for selectively connecting extremity biasing means between the lower frame to the middle frame for biasing the extremity angular position toward an extremity rest angle. The means for selectively connecting extremity biasing means preferably includes a plurality of eye members rigidly connected to each of the middle frame and the lower frame for sequentially connecting a plurality of biasing members therebetween, each of the biasing members providing a portion of a total biasing moment.

Further, the coupling means can include range limiting means for adjustably limiting a range of travel of the lower frame about the second hinge axis. Preferably the range limiting means includes cushion biasing means for cushioning a flexion limit of the range of travel.

The base can be adapted for supporting a foot of the user, and the second hinge means including right and left second hinge portions being located for straddling an ankle joint of the user. The brace can further include a pair of spaced apart heel anchor members fixably connected to the base of the lower frame, a cup shaped member for application to a heel portion of the user's foot, and means for supporting opposite extremities of the cup-shaped member from the heel anchor members, the cup-shaped member being located opposite the second hinge means from the heel anchor members for preventing movement of the heel portion away from the base. The extremities of the cup-shaped member can include flexible heel strap members, each extending ahead of one of the second hinge portions for support therefrom. Preferably, the base further includes an ankle pad member for axially supporting the ankle joint by a selected one of the hinge portions for selectively preventing eversion and inversion of the user's foot. Also, ankle fastener means can be included for adjustably connecting the ankle pad member to the hinge portion.

DRAWINGS

These and other features, aspects, and advantages of the present invention will become better understood with reference to the following description, appended claims, and accompanying drawings, where:

FIG. 1 is a side elevational view of an adjustable therapeutic limb brace according to the present invention;

FIG. 2 is a front elevational view of the brace of FIG. 1;

FIG. 3 is a bottom plan view of the brace of FIG. 1;

FIG. 4 is a sectional bottom plan view of the brace of FIG. 1 on line 4—4 of FIG. 2;

FIG. 5 is an exploded sectional view of the apparatus of FIG. 1 on line 5—5 of FIG. 4;

FIG. 6 is an exploded sectional view of the apparatus of FIG. 1 on line 6—6 of FIG. 2;

FIG. 7 is a left rear oblique elevational perspective detail view of the brace of FIG. 1;

FIG. 8 is a fragmentary side elevational view showing the brace of FIG. 1 in a flexed position; and FIG. 9 is a side elevational view showing an alternative configuration of the brace of FIG. 1;

FIG. 10 is a side elevational view showing another alternative configuration of the brace of FIG. 1;

FIG. 11 is a front elevational view showing further alternative configuration of the brace of FIG. 1;

FIG. 12 is a fragmentary side elevational view of the apparatus of FIG. 11.

DESCRIPTION

The present invention is directed to a therapeutic limb brace that is particularly versatile, effective, and easy to use. With reference to the drawings, and FIGS. 1-5 in particular, a brace apparatus 10 is applied to a user's limb or leg 11, the leg 11 including an upper limb or thigh 12, a lower limb or leg 14, and a limb extremity or foot 16, the thigh 12 and the lower leg 14 being joined by a limb joint or knee 18, the lower leg 14 and the foot 16 being joined by an extremity joint or ankle 20. The apparatus 10 includes an upper frame 22, a middle frame 24, and a lower frame 26, the upper and middle frames 22 and 24 being pivotably connected on a transverse first hinge or knee axis 28, the middle and lower frames 24 and 26 being pivotably connected on a transverse second hinge or ankle axis 30.

The upper frame 22 includes a spaced pair of elongate upper frame members 32a and lower frame members 32b, each upper frame member 32a being removably connected in selectable overlapping relation to a corresponding one of the lower frame members 32b. The frame members 32 and 32b are clamped in rigid axial alignment by, a plurality of frame fasteners 33 for forming an upper right frame 34 and an upper left frame 36, the length of the frames 34 and 36 being adjustable in increments 1 according to the spacing of a series of frame holes 37 in which the frame fasteners 33 are selectively located for fitting variously sized users. The upper right and left frames 34 and 36 are rigidly connected by an upper bridge member 38 that is fastened to the upper frame members 32a by counterparts of the frame fasteners 33, the bridge member 38 spacing apart the frames 34 and 36 sufficiently for generously clearing opposite sides of the user's thigh. The bridge member 38 includes a left bridge portion 38a and a right bridge portion 38b, the bridge portions 38a and 38b each having an array of bridge holes 39 and being removably connected in rigid overlapping relation to each other by additional ones of the frame fasteners 33 that engage selected pairs of the holes 39, thereby providing adjustable spacing between the upper right and left frames 34 and 36 for accommodating the thigh 12 of variously sized users. The upper frame 22 is secured to the user's thigh 12 by a pair of limb strap assemblies 40, designated 40a and 40b and further described below, the strap assemblies 40a and 40b locating the upper right and left frames 34 and 36 spaced away from opposite sides of the user's thigh 12.

In similar fashion, the middle frame 24 includes a spaced pair of elongate upper frame members 42a and lower frame members 42b, each upper frame member 42a being removably connected in selectable overlapping relation to a corresponding one of the lower frame members 42b by further counterparts of the frame fasteners 33, in rigid axial alignment therewith for forming a middle right frame 44 and a middle left frame 46, the frames 44 and 46 being thereby adjustable in length for fitting variously sized users. The middle right and left frames 44 and 46 are rigidly connected by a lower bridge member 48, the bridge member 48 spacing apart the frames 44 and 46 sufficiently for generously clearing opposite sides of the user's lower leg 14 and ankle 20. The bridge member 48 includes a left bridge portion 48a and a right bridge portion 48b, the bridge portions 48a and 48b being removably connected in selectable rigid overlapping relation to each other as described above in connection with the upper bridge member 38, thereby providing adjustable spacing between the upper left and right frames 44 and 46 for accommodating the lower leg 14 of variously sized users. The middle frame 24 is secured to the user's lower leg 14 by a further pair of limb strap assemblies 40, designated 40c and 40d, the strap assemblies 40c and 40d locating the upper left and right frames 44 and 46 spaced away from opposite sides of the user's lower leg 14.

The pivotable connection of the upper frame 22 to the middle frame 24 is by a pair of limb or knee pins 50, designated left knee pin 50a and right knee pin 50b, which connect, in overlapping relation, the lower frame members 32b of the upper frame 22 to the upper frame members 42a of the middle frame 24. Each of the frame members 32b of the upper frame 22 is formed to include an enlargement or plate member 52 having an arcuate array of index holes 54 therein. An upper extremity of each upper frame member 42a has a lock hole 56 whereby the middle frame 24 is lockable in a desired angular relation with the upper frame 22 by engagement of a lock pin 58 with the lock hole 56 and a selected one of the index holes 54 as indicated by the dashed lines in FIG. 1. A stop pin 60 is also provided proximate a lower extremity of the plate member 52 for preventing hyperextension of the middle frame 24 relative to the upper frame 22 when the lock pin 58 is not in use. Further, the lock pin 58 can be located in a selected one of the index holes 54 but not engaging the lock hole 56, for providing a desired range of movement. The range of movement can be between the lock pin 58 and the stop pin 60, or between a pair of the lock pins 58. Normally, one or a pair of the stop pins 60 is used in corresponding locations in each of the plate members 52.

In addition to the above, a variety of adjustable restraints can be connected between the upper frame 22 and the middle frame 24 as described herein, such connections being made from the lower bridge member 48 and a middle bridge member 62 that connects the plate members 52 as described above relative to the upper bridge member 38 and the lower bridge member 48, the middle bridge member 62 also having a left bridge portion 62a and a right bridge portion 62b for adjustably spacing the frames 22 and 24 from opposite sides of the user's knee 18. In particular, an anchor plate 64, which is rigidly connected to the middle bridge member 62 in a plurality of selectable positions, has mounted thereto one or more eye members 66, designated 66a, 66b, and 66c in the drawings. Similarly, one or more eye members 68, designated 68a, 68b, and 68c, are rigidly mounted to the lower bridge member 48, the eye members 68 also serving as the fasteners 33 between the bridge portions 48a and 48b. One or more extension springs 70, designated 70a, 70b, and 70c in FIG. 1, can be hooked over the respective eyes 66 and 68 for biasing the middle frame 24 as desired toward an extension position that is aligned with the upper frame 22, the middle frame 24 being arrested in its movement by engagement with the stop pins 60 of the upper frame 22 as further shown in FIG. 1. The biasing by the spring(s) 70 is further adjustable by selectively locating the anchor plate 64 relative to the middle bridge member 62.

As shown most clearly in FIGS. 2 and 4, each of the limb strap assemblies 40 includes a pair of limb straps 72, designated outer strap 72a and inner strap 72b, that extend in overlapping relation for enclosing the users limb or leg 11, the overlapping portions of the straps 72 being adjustably connected by loop and hook fastener means 74, as described herein. In particular, the strap assemblies 40a, 40c, and 40d are configured generally as shown in FIG. 4, the strap assembly 40b being described further below in connection with FIG. 6. Each of the limb straps 72 has a hook member 76 affixed along its outside face and a loop member 78 affixed along its opposite inside face as most clearly shown in FIG. 5. For anchoring the straps 72, an anchor strap 80 is affixed to each strap 72 by suitable means such as by sewing and/or riveting at spaced apart locations as indicated at 81 in FIG. 2, the anchor strap 80 extending from opposite sides of the limb strap 72, being affixed to the adjacent frame member 32 (or 42) by a pair of strap fasteners 82, such that when tension is applied to the connected limb strap 72, the anchor strap 80 is pulled slightly away from the frame member 32 (or 42). Another of the loop members, designated loop strap member 79 in the drawings, is sandwiched between the inner strap 72b and the connected anchor strap 80, the loop member 79 extending in opposite directions from the strap 80 and engaging the hook member 76 of the inner strap 72b for a portion of its length. The strap fasteners 82 engage selected ones of the frame holes 37, the holes 37 being preferably uniformly spaced substantially along the full length of the frame members 32 and 42 for interchangeably locating the bridge members 38 and 48 and the limb strap assemblies 40, as well as for fastening the overlapping counterparts of the frame members 32 and 42.

Each limb strap assembly 40 also includes a pad member 84 for attachment to the inside of the inner strap 72b and an exposed portion of the outer strap 72a, the pad member 84 having another of the hook members, designated 77 in the drawings, affixed along an outer substrate thereof. The pad member 84 distributes restraint force reactions about the user's limb 11 comfortably and longitudinally on opposite sides of the loop strap member 79.

A variation of the above described construction is used, as shown in FIG. 6, for the strap assembly 40b, for limiting lateral deflection of the user's knee 18. A disposition for lateral knee deflection is typically manifested in one direction only. Accordingly, the strap assembly 40b is adapted particularly for restraining against movement in one lateral direction, the opposite direction of restraint being obtained when necessary by inverting the strap assembly 40b. In particular, the outer limb strap 72a extends in one direction only about the user's limb 12 from the anchor strap 80. Also, the inner limb strap 72b is elongated to the point of overlapping itself. Thus, with the anchor strap 80 for the inner limb strap 72b selectively connected to the upper frame 22 on the side opposite the direction of potential lateral knee deflection, the strap 72b (together with the pad member 84) is snugly connected about the user's limb 12, the overlapping portion of the pad member 84 being tucked inside an outside portion thereof as indicated at 86 (instead of engaging the full length of the strap 72b). The degree of overlapping of the inner limb strap 72b upon itself is selected for a desired degree of restraint against the lateral movement of the user's knee 18. With the inner limb strap 72b thus adjusted, the outer limb strap 72a is then engaged therewith, the strap 72a being primarily employed for restraining against forward movement of the user's limb 12 at the strap assembly 40b. (In case restraint against rearward movement is needed, the outer strap 72a can be reversed for extension of the strap 72a rearwardly from the anchor strap 80.)

The limb strap assemblies 40 as described above are each openable and adjustable from both the front and the rear of the brace apparatus 10 for facilitating attachment and removal thereof, and for obtaining proper anterior-posterior alignment of the apparatus 10 relative to the user's limb 12, when the user is partially or completely immobilized, as well as for facilitating the attachment and removal by the user in appropriate cases.

As further shown in FIGS. 1-3, the lower frame 26 includes a foot-supporting plate or base member 88 having a pair of upstanding bars or column members 90 rigidly mounted thereon, the column members 90 being pivotally connected to the middle frame 24 by a pair of extremity or ankle pins 92, designated left ankle pin 92a and right ankle pin 92b. Further counterparts of the frame holes 37 are provided in the lower frame members 42b for receiving the ankle pins 92, these lowermost frame holes 37 being more closely spaced than the spacing 1 for accurately spacing the ankle pins 92 from the knee pins 50 according to the distance between the user's knee 18 and ankle 20.

A base pad member 93 covers the base member 88 for comfortably supporting the user's foot 16, the pad member 93 being protruded by the column members 90 for facilitating the rigid connection of the column members 90 to the base member 88. Also, an inside surface of each column member 90 has a column pad 94 affixed thereto. Further the column members 90 are each provided with a rectangular array of pin holes 95 for locating the ankle pins 92 to match the position of the user's ankle 20 relative to the columns 90. A pair of cleats 96, designated front cleat 96a and rear cleat 96b, are fastened to the underside of the base member 88 for support thereof and for elevating the user's foot 16 to conventional shoe height for ambulation. The cleats 96 are formed of a suitable resilient material such as NEOPRENE ® synthetic rubber for further cushioning of the user's foot and for protecting floor surfaces upon which the user may walk. The forward extremity of the base member 88 is angled upwardly for avoiding floor contact thereby when the user's foot 16 rocks forwardly on the front cleat 96a.

A pair of upwardly extending foot blocks 98 are rigidly connected to the base member 88 in a plurality of selectable positions for confining a front portion of the user's foot 16 therebetween. A front foot strap assembly 100 is provided for securing the foot 16 against the pad member 93, opposite ends of the strap assembly 100 being selectively affixed at one of a plurality of locations along the foot blocks 98 by a pair of strap fasteners 102. The strap assembly 100 includes a pair of strap members 104, designated 104a and 104b, that are adjustably connected by a buckle or loop member 107, the strap member 104b having counterparts of the hook and loop members 76 and 78 of the fastener means 74, designated generally as fastener means 106, the strap member 104b being doubled back onto itself and secured by the fastener means 106. A strap pad 108 is also removably affixed to the strap member 104b by another counterpart of the fastener means 106 for comfortable distribution of strap force reactions over the user's foot 16.

Similarly, a pair of upwardly extending heel blocks 110 are rigidly connected to the base member 88 in a plurality of selectable positions for confining a rear portion or heel 21 of the user's foot 16 therebetween as shown in FIGS. 1 and 7. In particular, each of the heel blocks 110 and the base mamber 88 are formed with a plurality of heel fastener passages 111, the passages 111 in the blocks 110 being laterally spaced differently than the passages 111 of the base 88 for permitting a "vernier" adjustment of the blocks 110. The heel blocks 110 are each formed to include a flange portion 112 for fastening to the base member 88, an upstanding wall portion 114, and an outwardly inclined ramp portion 116 for facilitating entry of the user's heel 21. The heel 21 is held proximately in contact with the pad member 94 by a heel strap assembly 118, opposite ends of the strap assembly 118 extending forwardly of the column members 90 and being rigidly connected to outside surfaces thereof by a plurality of the strap fasteners 102. The heel strap assembly 118 includes a heel strap member 120 having a heel cup member 122, the heel cup member 122 being formed by a downwardly extending dart connection 124 therein, and having a heel pad 126 therein for cushioning the user's heel 21. Adjustment of the heel strap assembly 118 is effected by engagement of the strap fasteners 102 selectively in a rectangular array of threaded fastener holes 128 that are formed in each of the column members 90. Also, the engagement of the ankle pins 92 with selected ones of the fastener holes 128 permits the ankle axis 30 to be located a proper distance above the base 88 for proximate alignment with the user's ankle 20. Further, one of the lowermost frame holes 37 is located in alignment with a corresponding one of the fastener holes 128 when the lower frame 26 is orthogonally aligned with the middle frame 24. Thus the lower frame 26 can be locked, when desired, in the orthogonal position by one or more suitable fasteners (not shown).

The user's foot 16 is also retained both downwardly against the pad member 94 and rearwardly against the heel strap assembly 118 by an instep strap assembly 130, opposite ends of which are anchored by the lowermost of the strap fasteners 102 that also anchor the heel strap assembly 118 to the outsides of the column members 90. The instep strap assembly 130 includes elongated counterparts of the strap members 104a and 104b, the fastener means 106, the loop member 107 and the strap pad member 108 of the front foot strap assembly 100.

The lower frame 26 is also provided with an ankle strap assembly 132 for selectively and adjustably limiting either inversion or eversion of the user's foot 16. The ankle strap assembly 132, which also includes counterparts of the strap members 104a and 104b, the fastener means 106, the loop member 107 and the strap pad 108, is anchored to front and rear edges of one of the column members 90, proximate one of the ankle pins 92, by additional ones of the strap fasteners 102. In particular, a pair of the fasteners 102 anchors the strap counterpart 104b to the front of the column member 90, but only one of the fasteners 102 is used for anchoring the strap counterpart 104a to the rear of the member 90 as further described herein. The ankle strap assembly 132 has an ankle cup member 133 slidably fastened thereon, the cup member 133 removably carrying an ankle pad 134 and being positioned against a selected lateral extremity of the user's ankle 20 for preventing movement thereof in a direction away from the column member 90 to which the ankle strap assembly 132 is anchored. Accordingly, with the ankle strap assembly 132 connected to the column member 90 which is visible on the right side of the brace apparatus 10 as shown in FIG. 1, eversion of the user's right foot 16 (or inversion of the left foot 16) is controllably prevented by appropriate adjustment of the fastener means 106 thereof. Likewise, eversion of the user's left foot 16 (or inversion of the right foot 16) is controllably prevented with the ankle strap assembly 132 inverted, being anchored to the column member 90 on the opposite (left) side of the lower frame 26. The use of only one of the fasteners 102 for anchoring the strap counterpart 104a of the ankle strap assembly 132 permits the counterpart 104a to pivot about the fastener 102 for further facilitating proper location of the strap assembly 132 with the ankle cup member 133 proximately centered against the user's ankle 20.

For limiting dorsiflexion and/or plantarflexion of the lower frame 26 (and the user's ankle 21), the brace apparatus 10 is provided with further counterparts of the eye members 66, including at least one eye member 135 on the lower bridge member 48, and at least one eye member 136 on the lower frame 26, the eye member 136 being mounted in one of a plurality of locations spaced along a top edge of one or both of the foot blocks 98. As shown in FIG. 1, one or more counterparts of the extension spring 70, designated extension spring 138 in FIG. 1, can be hooked over the respective eye members 135 and 136 for selectively adjustably biasing the lower frame 26 toward a dorsiflexed position.

With further reference to FIG. 8, an upper turnbuckle 140 can be connected between one of the eye members 66 and one of the eye members 68 for smoothly and forcibly moving the middle frame 24 relative to the upper frame 22. The turnbuckle 140 is advantageously effective in slowly overcoming a contracture of the user's leg 11. Once in position, the turnbuckle 140 can be left in place. Alternatively, the turnbuckle 140 can be adjusted for alignment of the lock hole 56 with one of the index holes 54; then, the lock pin 58 can be used for locking the middle frame 24 in the position obtained by the turnbuckle 140, and the turnbuckle 140 can be disengaged or removed completely, if desired.

Similarly, a lower turnbuckle 142 can be connected between an eye member 135 of the middle frame 24 and an eye member 136 of the lower frame 26 for smoothly and forcibly moving the lower frame 26 relative to the middle frame 24. The turnbuckle 142 is advantageously effective in slowly overcoming a contracture of the anterior or posterior muscles of the user's lower leg 14.

In use, the upper and middle frames 22 and 24 are adjusted in length and lateral spacing by appropriate selection of the frame holes 37 and bridge holes 39 to which the frame fasteners 33 are engaged as described above, and the strap assemblies are similarly affixed by the strap fasteners 82 in spaced apart locations on each of the upper and lower frames 22 and 26, whereby the knee axis 28 approximately coincides with the fulcrum of the user's knee 18, and the bottom of the middle frame 24 is slightly below the user's ankle 20 such that one pair of the frame holes 37 is approximately aligned with the fulcrum of the user's ankle 20. The tops of the upper frame 22 are preferably located from approximately 2 inches to approximately 4 inches below the top of the user's thigh. Next, the user's foot is fitted to the lower frame 26, and the ankle pins 92 are connected between the previously identified frame holes 37 and a pair of the pin holes 95 of the column members 90 that are most closely aligned with the user's ankle 20, appropriate spacers being used if necessary (and longer counterparts of the ankle pins 92) between the lower frame members 42b and the column members 90. The foot blocks 98 are positioned, if necessary, on the base member 88 for accommodating the ball of the user's foot 16, and the heel blocks 110 are similarly adjusted for receiving the user's heel 21. The adjustment of the heel blocks 110 in small increments is facilitated by the differently spaced patterns of the heel fastener passages 111 in the blocks 110 and in the base 88 as described above. The location of the foot strap assembly 100 on the foot blocks 98 is adjusted, if necessary, for locating the strap pad 108 over the ball of the user's foot 16, not the toes. With the frames 22, 24, and 26 thus assembled, the strap assemblies 40, 100, 118, 130 are secured and, if necessary for support against inversion or eversion of the foot 16, the ankle strap assembly 132 is connected and adjusted as described above. As noted above, the upper and middle frames 22 and 24 can be secured and the strap assemblies 40 adjusted, if necessary, with the user accessible from only the front or the rear. Advantageously, the strap assemblies 40 locate the frames 22 and 24 firmly, yet resiliently relative to the user's thigh 12 and lower leg 14, in that the assemblies 40b and 40c are spaced slightly on opposite sides of the user's knee. Thus the knee pins 50 which define the knee axis 28 suitably approximate the motion of the user's knee 18, in that the fulcrum of the knee 18 is only approximately fixed relative to the thigh 12 and the lower leg 14. Accordingly, the movement of the middle frame 24 relative to the upper frame 22 accurately corresponds to the movement of the user's knee 18, yet without binding, and without requiring a complex knee pivot mechanism. Similarly, the location of the limb strap assembly 40d slightly above the user's ankle 20 provides close correspondence between movement of the lower frame 26 relative to the middle frame 24 and movement of the user's ankle 20.

Once the frame assemblies 22, 24, and 26, are adjusted and applied as described above, appropriate controls for movement of the user's knee 18 and ankle 20 are activated as also described above, depending on the user's condition and the progress of therapy. Preferably several of the springs 70 are provided for dynamic adjustment of biasing of the user's knee 18, by selection therefrom of one, two, or three of the springs 70 to make up a desired total of the biasing. Advantageously, only one of the springs 70 need be tensioned and connected at a time, so that the effort in extending and connecting any one of the springs 70 can be significantly less than what would be required for the total of the biasing to be supplied by only one of the springs 70. Further, the eye members 68 are selectively locatable on the lower bridge member 48, and the eye members 66 are selectively locatable by positioning the anchor plate 64 relative to the middle bridge member 62. Similarly, the biasing of the lower frame 26 can be by a selection of one or two from a plurality of the extension springs 138. Moreover, the eye members 136 are selectively locatable on the foot blocks 98, and the eye members 135 are selectively locatable on the lower bridge member 48.

With further reference to FIG. 9, an alternative means for adjustably biasing the middle frame 24 relative to the upper frame 22 is provided by a tackle assembly 144 that is substituted for the eye members 68 and springs 70 of FIG. 1. As shown in FIG. 9, a first extension spring 146 is connected to the eye member 66c that is located on the anchor plate 64 of the upper frame 22, the spring 146 being serially connected to a flexible tension member or first cable 148, the cable 148 extending downwardly and engaging the underside of a lower sheave 150 that is rotatably mounted to the lower bridge member 48 of the middle frame 24. From the lower sheave 150, the first cable 148 extends upwardly, being serially connected to a second extension spring 152 and a second cable 154, the cable 154 engaging a middle sheave 156 that is rotatably mounted to the anchor plate 64. From the middle sheave 156, the cable 154 continues upwardly to a point of attachment with a third extension spring 158 that is also serially connected to a third cable 160, the cable 160 passing over an upper sheave 162 that is rotatably mounted to the upper bridge member 38, from which the third cable extends downwardly, being adjustably anchored to the anchor plate 64 by a tackle turnbuckle 164 that is hooked to another of the eye members, designated eye member 166, the eye member 166 being rigidly mounted to the anchor plate 64.

The tackle assembly 144 advantageously provides a continuous adjustment of the biasing force between the upper and middle frames 22 and 24 by means of the tackle turnbuckle 164, the turnbuckle 164 being conveniently located for adjustment, proximate the user's thigh 12. Similarly, the brace apparatus 10 is advantageously adapted for donning and activation by the user in that the tackle assembly 144 may be activated by completing any one of the serial connections described above, such as by hooking the tackle turnbuckle 164 onto the eye member 166. This connection is facilitated in that the parts to be connected, such as the tackle turnbuckle 164 and the eye member 166 are conveniently located above the user's knee 18, and in plain view. Moreover, the connection is facilitated by a two-to-one mechanical advantage that is associated with the lower sheave 150.

With further reference to FIG. 10, a preferred alternative configuration of the tackle assembly 144 has the lower sheave 150 and the upper sheave 162 mounted transversely for providing a more compact arrangement. The lower bridge member 48 is angled slightly downwardly from the lower frame 26 for locating the lower sheave 150 in a plane that proximately bisects the path of the first cable 148 on opposite sides of the sheave 150. Similarly, the middle sheave 156 and the eye member 166 locate the path of the second cable 154 symmetrically slightly on opposite sides of the plane of the upper sheave 162. The cables 148 and 154, which can be stranded stainless steel cable having an outside diameter of approximately 0.06 inch, smoothly engage the sheaves 150 and 162 by virtue of a somewhat oversize, trough-shaped groove configuration (approximately 0.2 inch wide) of the sheave 150 and 162. Ball-bearing wheels having an outside diameter of approximately 1.5 inches, that are typically used for supporting conventional sliding doors are suitable for use as the sheaves 150 and 162 in the present invention. As further shown in FIG. 10, the middle sheave 156 is rotatably mounted within a housing or block 157. The sheave 156, having an outside diameter of approximately 1.0 inch, is readily available assembled with the block 157 as a standard hardware item.

As also shown in FIG. 10, the stp pin 60 is relocated in the upper frame 22 above the knee axis 28, the upper frame members 42a of the middle frame 24 are formed with a rearwardly facing stop notch 61 for engaging the stop pin 60 when the middle frame 24 is fully extended relative to the upper frame 22.

As further shown in FIG. 10, the apparatus 10 is provided with a limit cushion assembly 170 pivotably connected between the middle frame 24 and the lower frame 26. The cushion assembly 170 has a flanged cylindrical piston member 172 that threadingly engages an elongated eye member 174, the eye member 174 being pivotably connected to one of the foot blocks 98 of the lower frame 26 by an eye screw 175. The piston member 172 slidingly engages a sleeve member 176 that is similarly connected to the middle frame 24 by another of the eye members 174. A limit pin 178, that rigidly protrudes the piston member 172, extends into a longitudinal slot 180 of the sleeve member 176. The length of the slot 180 is selected for limiting a range of travel of the lower frame 26 about the ankle axis 30, the relative position of the range being determined by appropriate adjustment of the threaded engagement of the eye members 174. Further, the range of travel is selectably adjustable according to the location of the eye screw 175 in the foot block 98. Alternatively, the limit cushion assembly 170 can be configured for adjustment of the effective length of the slot 180, such as by a slot spacer 182 that removably engages the slot 180. The cushion assembly 170 also includes a cushion spring 184 on the piston member 172, the spring 184 engaging the sleeve member 176 as the upper travel limit of the assembly 170 is approached. Thus the limit cushion assembly 170 provides a cushioned upper travel limit to movement of the lower frame 26 about the ankle axis 30, for walking. Typically, the extension spring 138 is configured for biasing against downward movement of the base member 88 below an approximately orthogonal inclination of the base member 88 relative to the middle frame 24. The upper limit of the cushion assembly can be set at approximately 30° above the orthogonal position, a range of free travel being provided between inclinations at which the extension spring 138 and the cushion spring 184 are operative.

With further reference to FIGS. 11 and 12, another preferred alternative configuration of the apparatus 10 has a dual version of the tackle assembly 144, including a pair of the upper sheaves 162 and a pair of the middle sheaves 156, the middle sheaves 156 each being mounted in a corresponding block 157. As shown in FIG. 11, a spacer block 188 being also fastened between the left and right upper bridge portions 38a and 38b for rigidly securing the bridge member 38. In this configuration, the first cable 148, and the lower sheave 150 are not used, two of the second extension springs 152 being directly anchored to the lower bridge member 48 by the eye members 68a and 68b. The extension members are each series-connected to counterparts of the second cable 154, the third extension spring 158, and the middle sheave 156, the middle sheave 156 being tied together and anchored through single counterparts of the first extension spring 146 and the tackle turnbuckle 164 to the eye 166. This configuration of the tackle assembly 144 advantageously provides staged engagement between the upper frame 22 and the middle frame 24 for facilitating the engagement and adjustment of the tackle assembly 144, especially by the user. The common connection through the single turnbuckle 164 further facilitates the adjustment. Moreover, further staged biasing connections are available from the extension springs 70a and 70b that can be connected between the eyes 66a and 66b on the bridge member 62 (conveniently connected into the blocks 157 as shown in FIGS. 11 and 12), and eyes 68c and 68d that are fastened on opposite sides of the bridge 48.

Another and important advantage of the combination of the extension springs 70 with the tackle assembly 144 is that a bias profile associated with the springs 70 is fortuitously complementary with a bias profile that is associated with the tackle assembly 144. In particular, although the extension springs 146, 152 and 158 of the tackle assembly 144, as well as the extension springs 70, have an essentially linear force-deflection characteristic, the geometry of the apparatus 10 results in a nonlinear biasing moment about the knee axis 28. However, the nonlinearities associated with the biasing by the tackle assembly 144 and by the extension springs 70 tend to favorably cancel, the extension springs 70 contributing to a relatively high available biasing moment in a range of movement at and approaching the fully extended position of the middle frame 24 relative to the upper frame 22. This high level of available biasing moment is particularly advantageous proximate the extended position because conventional therapeutic apparatus such as splints becomes ineffective when the limb 12 approaches full extension.

As further shown in FIGS. 11 and 12, another counterpart of the bridge members, designated foot bridge 186, can be connected between the foot blocks 98 of the lower frame 26, the foot bridge 186 having overlapping left and right bridge members, 186a and 186b, for accommodating the alternative spacings between the foot blocks 98 as described above in connection with the bridge members 38, 48, and 62. The foot bridge 186 provides a convenient upper travel limit or stop for the lower frame 26, such as by engagement of a frame fastener 33 (that connects the bridge members 186a and 186b) against the ankle bridge 48, thereby limiting an upward flexion of the user's foot when walking.

The adjustable configuration of the lower frame 26 advantageously adapts the apparatus 10 for use with ambulatory patients, without requiring a shoe of the user to be sacrificed by bolting the shoe into the lower frame 26. Moreover, the frame 26 can be conveniently configured for walking with or without a shoe of the user.

Although the present invention has been described in considerable detail with reference to certain preferred versions thereof, other versions are possible. For example, the upper frame 22 and the middle frame 24 can be adapted for use on the user's arm, the first hinge axis 28 functioning as an elbow axis. Also, the eye member 166 of the tackle assembly 144 can be relocated to the upper bridge member 48, replacing the upper sheave 162, and permitting the tackle turnbuckle 164 to be directly connected to the third extension spring 158, replacing the third cable 160. Further, [turnbuckle 140 can be used to flex the knee as well as extend it with various length turnbuckles.] Therefore, the spirit and scope of the appended claims should not necessarily be limited to the description of the preferred versions contained herein.

What is claimed is:

1. An adjustable therapeutic brace comprising:
   (a) an upper frame comprising:
      (i) right and left rigid upper frame portions;
      (ii) at least one rigid upper cross frame portion for rigidly connecting the upper frame portions in parallel spaced relation;
      (iii) means for connecting the upper frame portions in spaced relation to opposite sides of an upper limb portion of a user;
   (b) a middle frame comprising:
      (i) right and left rigid middle frame portions;
      (ii) at least one rigid middle cross frame portion rigidly connecting the middle frame portions in parallel spaced relation;
      (iii) means for connecting the middle frame portions in spaced relation to opposite sides of a middle limb portion of the user;
   (c) right and left first hinge means for pivotally connecting the upper frame to the middle frame relative to a first hinge axis, the middle frame being movable from a flexion position to an extension position relative to the upper frame, the first hinge axis being located for intersecting a first limb joint of the user; and
   (d) first limiting means for selectively limiting movement of the middle frame about the first hinge axis relative to the upper frame comprising first sheave means and tension means mounted between the right and left frame portions.

2. The apparatus of claim 1 wherein at least one of the upper and middle frame portions comprises an upper frame member and a lower frame member, and means for selectively rigidly connecting the frame members in overlapping parallel relation for obtaining a desired effective length of the upper and middle frame portions.

3. The apparatus of claim 1, wherein each of the cross frame portions includes means for selectively defining a separation between opposite ends thereof for adjustably spacing the frame portions from the user's limb portions.

4. The apparatus of claim 1, wherein the means for connecting the frame portions relative to the user's limb portions comprises a plurality of spaced apart limb strap assemblies connected to each of the upper and middle frame portions.

5. The apparatus of claim 4, wherein at least some of the limb strap assemblies each comprise front and rear adjustable buckle means for providing opening and closure of the respective strap assemblies, as well as adjustment of same, selectively from both the front and rear of the user.

6. The apparatus of claim 4, wherein each of at least some of the limb strap assemblies comprises:
   (a) an adjustable limb strap for enclosing the limb portion; and
   (b) a pair of anchor straps, each anchor strap connecting the limb strap to one of the right and left frame portions for support of the limb strap in spaced relation to the frame portions.

7. The apparatus of claim 1, wherein the first limiting means comprises means for selectively locking the first hinge means into one of a plurality of angularly spaced positions.

8. The apparatus of claim 7, wherein the means for selectively locking the first hinge means comprises:
   (a) a plate member fixed on one of the upper and middle frames, the plate member forming a plurality of spaced engagement surfaces, the engagement surfaces being equidistant from the first hinge axis; and
   (b) means for locating an engagement member in fixed relation to the other of the upper and middle frames, the engagement member being in locating engagement with a selected one of the engagement surfaces.

9. The apparatus of claim 8, wherein each of the upper frame portions forms one of the plate members, and each of the middle frame portions includes means for locating the corresponding engagement members.

10. The apparatus of claim 9, wherein the means for locating the engagement members comprises an engagement passage in each of the middle frame portions, the engagement passage being located in line with the upper frame in the extension position, and opposite the first hinge axis from the means for connecting the middle frame portions to the middle limb portion.

11. The apparatus of claim 8, wherein each of the engagement surfaces forms a cylindrical passage between opposite sides of one of the frame portions.

12. The apparatus of claim 1, wherein the first limiting means comprises means for selectively connecting extension biasing means between the upper frame and the middle frame for urging the middle frame toward the extension position.

13. The apparatus of claim 12, wherein the means for selectively connecting extension biasing means comprises:
   (a) first sheave means mounted to one of the upper and middle frames between the right and left frame portions thereof, and offset from the first hinge axis for clearing the user's limb;
   (b) a flexible tension member movably engaging the sheave means;
   (c) a first biasing member connected between the tension member and one of the upper and middle frames; and
   (d) means for connecting the tension member to the other of the upper and middle frames.

14. The apparatus of claim 13, comprising at least two parallel-connected counterparts of the series-connected first sheave means, the tension member, and one of the first biasing members.

15. The apparatus of claim 1, further comprising stop means for preventing movement of the middle frame beyond a stop extremity angle about the first hinge axis relative to the upper frame.

16. The apparatus of claim 15, wherein the stop means comprises a stop member on one of the upper and middle frames, the stop member engaging the other of the frames in the extension position.

17. The apparatus of claim 15, wherein the stop means comprises:
   (a) a plate member fixed on one of the upper and middle frames, the plate member forming a plurality of spaced engagement surfaces; and
   (b) a stop member for engagement by a selected one of the engagement surfaces, the stop member preventing movement of the other frame member in one direction relative thereto by contact therewith.

18. The apparatus of claim 1, further comprising a lower frame connected to the middle frame, the lower frame including a base for supporting a limb extremity of the user.

19. The apparatus of claim 18, further comprising second hinge means whereby the lower frame is pivotably connected to the middle frame relative to a second hinge axis.

20. The apparatus of claim 19, wherein an effective length of the middle frame portion is changeable for selecting a desired distance between the first hinge axis and the second hinge axis.

21. The apparatus of claim 19, further comprising means for controlling an extremity angular position of the lower frame relative to the middle frame about the second hinge axis.

22. The apparatus of claim 21, wherein the means for controlling the lower frame comprises coupling means for connecting the lower frame and the middle frame along a coupling axis, the coupling axis being displaced to one side of the second hinge axis and having a connection component in a plane normal to the second hinge axis.

23. The apparatus of claim 22, wherein the coupling means comprises a turnbuckle assembly, the turnbuckle assembly being pivotally connected between the lower frame and the middle frame for locking the lower frame in a predetermined angular position relative to the middle frame.

24. The apparatus of claim 22, wherein the coupling means comprises means for selectively connecting extremity biasing means between the lower frame to the middle frame for biasing the extremity angular position toward an extremity rest angle.

25. The apparatus of claim 24, wherein the means for selectively connecting extremity biasing means comprises a plurality of eye members rigidly connected to each of the middle frame and the lower frame for sequentially connecting a plurality of biasing members therebetween, each of the biasing members providing a portion of a total biasing moment.

26. The apparatus of claim 22, wherein the coupling means comprises range limiting means for adjustably limiting a range of travel of the base about the second hinge axis.

27. The apparatus of claim 26, wherein the range limiting means comprises cushion biasing means for cushioning a flexion limit of the range of travel of the base about the second hinge axis.

28. The apparatus of claim 19, wherein the base is adapted for supporting a foot of the user, the second hinge means including right and left second hinge portions, the second hinge portions being located for straddling an ankle joint of the user.

29. An adjustable therapeutic brace comprising:
   (a) an upper frame comprising:
      (i) right and left upper frame portions; and
      (ii) means for connecting the upper frame portions in spaced relation to opposite sides of an upper limb portion of a user;
   (b) a middle frame comprising:
      (i) right and left middle frame portions; and
      (ii) means for connecting the middle frame portions in spaced relation to opposite sides of a middle limb portion of the user;
   (c) right and left first hinge means for pivotally connecting the upper frame to the middle frame relative to a first hinge axis, the middle frame being movable from a flexion position to an extension position relative to the upper frame; and
   (d) first limiting means for selectively limiting movement of the middle frame about the first hinge axis relative to the upper frame, the first limiting means comprising means for selectively connecting extension biasing means between the upper frame and the middle frame for urging the middle frame toward the extension position, the means for selectively connecting extension biasing means comprising:
      (i) first sheave means mounted in fixed relation to one of the upper and middle frames and the axis of which is offset from the first hinge axis;
      (ii) a flexible tension member movably engaging the sheave means;
      (iii) a first biasing member connected between the tension member and one of the upper and middle frames;
      (iv) means for connecting the tension member to the other of the upper and middle frames;
      (v) second sheave means fixedly located on the other of the upper and middle frames and spaced from the first sheave means, the tension member movably engaging the second sheave means; and
      (vi) a second biasing member connected between the tension member and the one of the upper and middle frames.

30. The apparatus of claim 29, further comprising turnbuckle means connected in series with the tension member for adjusting an overall length of the tension member and the biasing members of the extension biasing means.

31. The apparatus of claim 29, further comprising third sheave means fixedly located on the one of the upper and middle frames and spaced from the first sheave means, the tension member movably engaging the third sheave means.

32. An adjustable therapeutic brace comprising:
   (a) an upper frame comprising:
      (i) right and left upper frame portions; and
      (ii) means for connecting the upper frame portions in spaced relation to opposite sides of an upper limb portion of a user;
   (b) a middle frame comprising:
      (i) right and left middle frame portions; and
      (ii) means for connecting the middle frame portions in spaced relation to opposite sides of a middle limb portion of the user;
   (c) right and left first hinge means for pivotally connecting the upper frame to the middle frame relative to a first hinge axis, the middle frame being movable from a flexion position to an extension position relative to the upper frame;
   (d) first limiting means for selectively limiting movement of the middle frame about the first hinge axis relative to the upper frame comprising first sheave means and tension means mounted between the right and left frame portions;
   (e) a lower frame connected to the middle frame, the lower frame including a base for supporting a foot of the user;
   (f) second hinge means whereby the lower frame is pivotably connected to the middle frame relative to a second hinge axis, the second hinge means including right and left second hinge portions, the second hinge portions being located for straddling an ankle joint of the user;
   (g) a pair of spaced apart heel anchor members fixably connected to the base of the lower frame;
   (h) a cup-shaped member for application to a heel portion of the user's foot; and
   (i) means for supporting opposite extremities of the cup-shaped member from the heel anchor members, the cup-shaped member being located opposite the second hinge means from the heel anchor members for preventing movement of the heel portion away from the base.

33. The apparatus of claim 32, further comprising means for adjusting a distance between the cup-shaped member and the second hinge axis, including a pair of flexible heel strap members connected to the cup-shaped member, each heel strap member extending ahead of one of the second hinge portions for support therefrom.

34. An adjustable therapeutic brace comprising:
   (a) an upper frame comprising:
      (i) right and left upper frame portions; and
      (ii) means for connecting the upper frame portions in spaced relation to opposite sides of an upper limb portion of a user;
   (b) a middle frame comprising:
      (i) right and left middle frame portions; and
      (ii) means for connecting the middle frame portions in spaced relation to opposite sides of a middle limb portion of the user;
   (c) right and left first hinge means for pivotally connecting the upper frame to the middle frame relative to a first hinge axis, the middle frame being movable from a flexion position to an extension position relative to the upper frame;
   (d) first limiting means for selectively limiting movement of the middle frame about the first hinge axis relative to the upper frame comprising first sheave means and tension means mounted between the right and left frame portions;
   (e) a lower frame connected to the middle frame, the lower frame including a base for supporting a foot of the user;
   (f) second hinge means whereby the lower frame is pivotably connected to the middle frame relative to a second hinge axis, the second hinge means including right and left second hinge portions, the second hinge portions being located for straddling an ankle joint of the user; and
   (g) an ankle pad member for axially supporting the ankle joint from a selected one of the hinge portions, for selectively preventing eversion and inversion of the user's foot.

35. The apparatus of claim 34, further comprising ankle fastener means for adjustably connecting the ankle pad member to the hinge portion.

* * * * *